United States Patent
Nishii et al.

(10) Patent No.: US 7,393,328 B2
(45) Date of Patent: Jul. 1, 2008

(54) PHYSICAL CONDITION MONITORING SYSTEM

(75) Inventors: Katsuyoshi Nishii, Okazaki (JP); Teiyuu Kimura, Nagoya (JP); Kazuhiro Sakai, Anjo (JP); Masaaki Sugita, 1-10-4, Yumegaoka, Tsu-city, Mie-pref., 514-0116 (JP)

(73) Assignees: DENSO CORPORATION, Kariya (JP); Masaaki Sugita, Mie-pref. (JP)

( * ) Notice: Subject to any disclaimer, the term of this patent is extended or adjusted under 35 U.S.C. 154(b) by 429 days.

(21) Appl. No.: 10/944,718

(22) Filed: Sep. 21, 2004

(65) Prior Publication Data

US 2005/0080344 A1 Apr. 14, 2005

(30) Foreign Application Priority Data

Oct. 10, 2003 (JP) ............................. 2003-352493

(51) Int. Cl.
*A61B 5/02* (2006.01)

(52) U.S. Cl. .................... 600/500; 600/483; 600/481

(58) Field of Classification Search ................. 600/300, 600/301, 481, 483–485, 490–504, 506, 507
See application file for complete search history.

(56) References Cited

U.S. PATENT DOCUMENTS

| | | | |
|---|---|---|---|
| 6,261,235 B1 * | 7/2001 | Amano et al. | 600/485 |
| 6,364,842 B1 * | 4/2002 | Amano et al. | 600/485 |
| 6,767,329 B2 * | 7/2004 | Amano et al. | 600/500 |
| 6,786,866 B2 * | 9/2004 | Odagiri et al. | 600/300 |
| 7,160,253 B2 * | 1/2007 | Nissila | 600/500 |
| 2004/0152957 A1 * | 8/2004 | Stivoric et al. | 600/300 |
| 2005/0148894 A1 * | 7/2005 | Misczynski et al. | 600/513 |
| 2006/0247542 A1 * | 11/2006 | Watanabe et al. | 600/500 |

FOREIGN PATENT DOCUMENTS

JP A-11-137539 5/1999

* cited by examiner

*Primary Examiner*—Charles Marmor, II
*Assistant Examiner*—Navin Natnithithadha
(74) *Attorney, Agent, or Firm*—Posz Law Group, PLC (57) ABSTRACT

A microcomputer included in a physical condition monitoring system calculates the amount of autonomic nerve activity during sleep based on physical information during sleep collected by a physical information collecting device 1. The physical information contains heart rates, blood pressure, respiratory rate, and the amount of body movement. The microcomputer also receives various kinds of information including training conditions via an input device. Then, it displays the amount of autonomic nerve activity and the training conditions on a display device in a manner that connections between them are indicated.

15 Claims, 9 Drawing Sheets

PHYSICAL CONDITION MONITORING SYSTEM

CROSS REFERENCE TO RELATED APPLICATION

This application is based on and incorporates herein by reference Japanese Patent Application No. 2003-352493 filed on Oct. 10, 2003.

FIELD OF THE INVENTION

The present invention relates to a physical condition monitoring system.

BACKGROUND OF THE INVENTION

Figure 10:
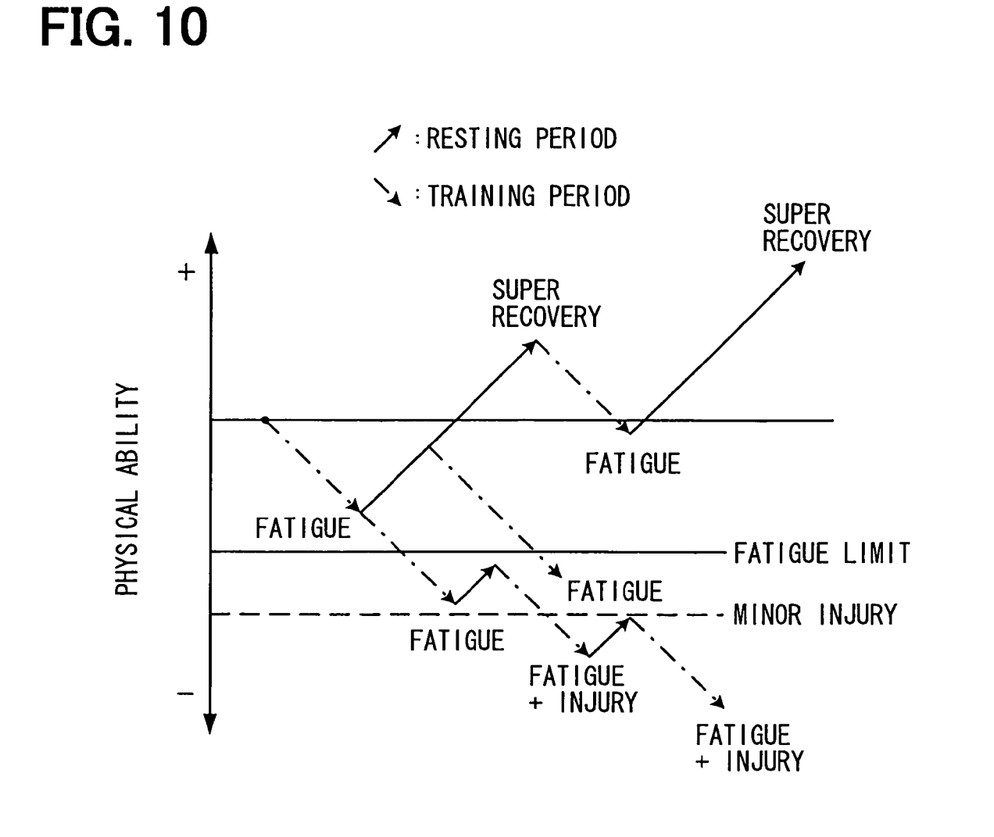
FIG. 10 is a graph showing connections between fatigue, recovery, physical ability, and overtraining.

In a process of building physical abilities, athletes temporarily experience underperformance after heavy training. However, their physical abilities improve during a process of recovery from fatigues caused by the training. This phenomenon is known as super recovery. If the athletes continue heavy training without rest, fatigue builds up and may result in injury when a level of the fatigue exceeds their fatigue limit. Athletes are more likely to develop a physical disorder called an overtraining syndrome under such conditions. Physical abilities improve or degrade according to fatigue or recovery as shown in FIG. 10.

The overtraining syndrome is a phenomenon that athletic abilities of athletes decrease due to lack of balance between training load and rest. Symptoms of minor injury are difficult to distinguish from fatigue. If the minor injury is not noticed and the training is continued, the symptoms of minor injury may become worse. As a result, the athlete may fall in a serious physical condition, from which it is difficult to recover. It may take over a year for an athlete to recover from serious injury while it normally takes a few days to recover from minor injury. Therefore, it is very important to properly monitor physical conditions of athletes to prevent overtraining.

The amount of training, the amount of rest, and the performance of athletes during training are usually used as indexes for determination of overtraining. However, it is difficult to detect overtraining based on these indexes because an ability to cope with fatigue, a fatigue limit, or a level of recovery differs from athlete to athlete. Namely, it is difficult to determine overtraining based on standardized indexes and the overtraining determination greatly depends on experiences of trainers.

To objectively determine a level of recovery or a level of fatigue, heart rate, or pulse rate, and temperature after waking up in the morning are used as indexes in addition to the above-described indexes. However, such heart rate and the temperature greatly vary according to a wake-up condition, for instance, waking up in hurry or frightened by an alarm clock. Thus, accurate determination of levels of rest and recovery after sleep cannot be made based on the heart rate and the temperature after waking up.

An apparatus for detecting overuse of muscles of lower limbs is proposed in JP-A-11-137539. In this apparatus, shock absorbing capabilities of the lower limbs during running are measured and overuse of the muscles is determined based on a decrease in the capabilities. Namely, it only determines whether temporary fatigue in the lower limbs during training exceeds the limit but not properly detect signs or symptoms of overtraining resulting from an accumulation of fatigue.

The sufficient amount of rest is required before starting training again when an athlete has recovered from overtraining. Thus, it is important to understand a level of recovery of the athlete from the overtraining. However, the level of recovery is not accurately detected by known methods.

SUMMARY OF THE INVENTION

The present invention therefore has an objective to provide a physical condition monitoring system that detects signs or symptoms of overtraining and accurately detects levels of recovery from overtraining. A physical condition monitoring system of the present invention includes physical information collecting means, raining information collecting means, and display means.

The physical information collecting means collects physical information indicating a physical condition of a subject during sleep. The physical information is produced through analysis of a pulse wave. A pulse rate or the amount of autonomic nerve activity may be used as the physical information during sleep. The training information colleting means collects training information indicating a training condition. The display means displays the physical information obtained by the physical information collecting means and the training information obtained by the training information collecting means, such that they are associated with each other.

With this configuration, connections between the physical conditions of the subject during sleep (physical information during sleep) and the training condition (training information) are easily determined. The physical conditions of the subject, especially sings or symptoms of overtraining, or levels of recovery from overtraining are properly determined referring to the connections.

The physical condition monitoring system further includes storage means that stores multiple days of the physical information and the training information. The display means displays multiple days of the physical information and the training information stored in the storage means so that variations in the information are recognized. The physical conditions of the subject are more accurately determined through observations of the variations.

The physical condition monitoring system still further includes physical condition determining means that determines physical conditions of the subject based on the physical information during sleep and the training information. The display means displays a result of the determination together with the physical information and the training information. Namely, the physical condition of the subject is quantitatively determined based on the physical information and the training information and the result of the determination is displayed. Therefore, sings or symptoms of overtraining are properly detected.

BRIEF DESCRIPTION OF THE DRAWINGS

The above and other objectives, features and advantages of the present invention will become more apparent from the following detailed description made with reference to the accompanying drawings. In the drawings.

DETAILED DESCRIPTION OF THE PREFERRED EMBODIMENT

The preferred embodiments of the present invention will be explained with reference to the accompanying drawings. To understand the present invention, connections between levels of fatigue due to training, the amounts of sympathetic nerve activities and parasympathetic nerve activities during sleep, and heart rates during sleep will be discussed referring to FIG. 9.

When physical strength remains in a body, namely, a fatigue level is low, the amount of parasympathetic nerve activity (HF) increases to rest the body and reduce energy consumption. After heavy-load training and the body feels strains, that is, temporary fatigue, the amount of sympathetic nerve activity (LF/HF) increases. As a result, heart rates (HR) increase even during sleep, for instance, on day T3, T4 in FIG. 9. When the heavy-load training continues and fatigue builds up in the body, the body shows a reaction to actively take rest. More specifically, the amount of parasympathetic nerve activity increases during sleep on a resting day, for instance, on day R3, R4. This symptom is normally diagnosed as sympathetic overtraining, or Basedowic overtraining.

Figure 9:
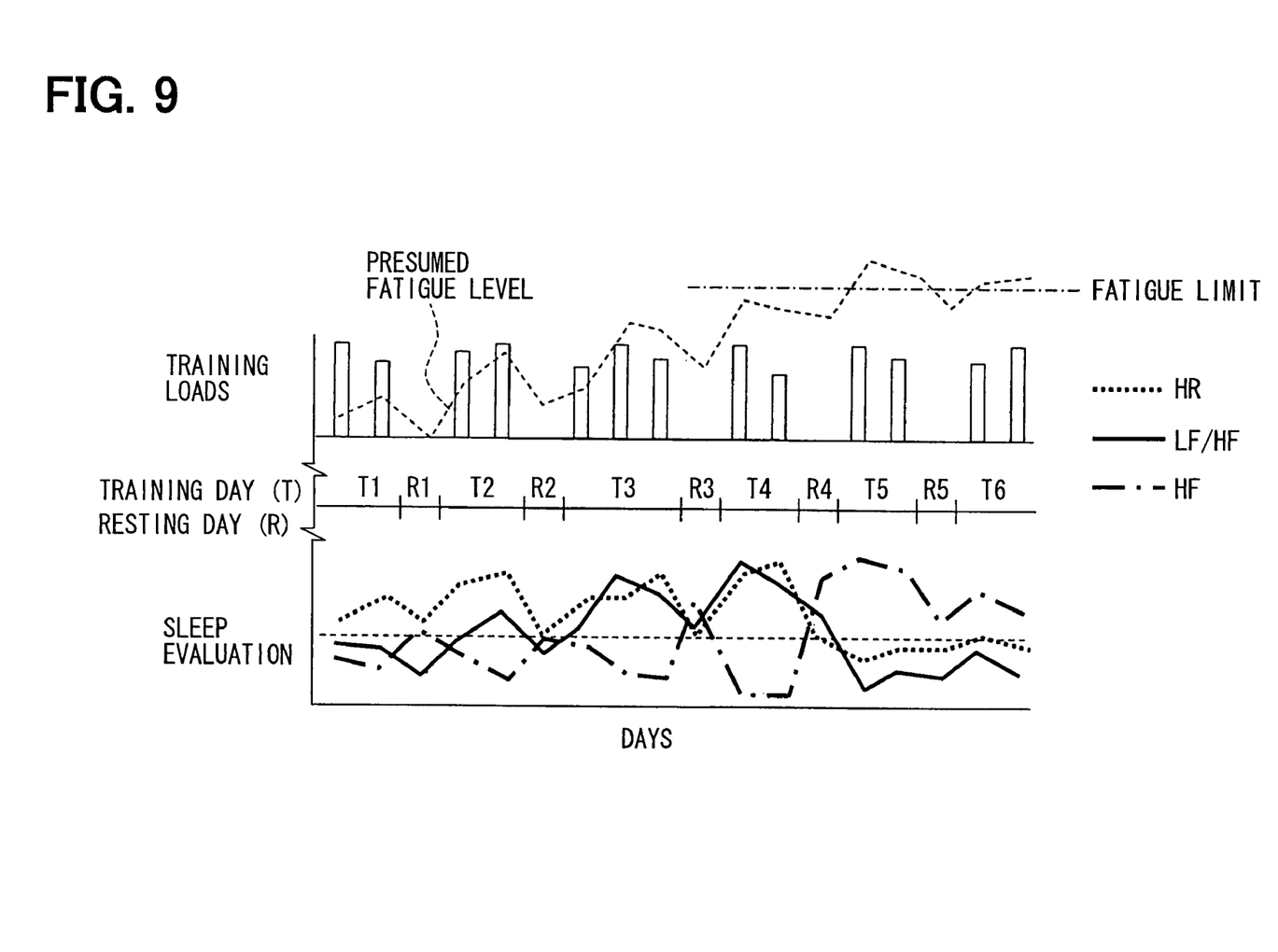
FIG. 9 is a graph showing connections between training conditions and the amount of autonomic nerve activity.

If the temporary fatigue continuously builds up, a reverse phenomenon in the amount of the autonomic nerve activity at a certain time is observed after the body has received loads in training. A large increase in the amount of parasympathetic activity is observed in a condition that an increase in the amount of sympathetic nerve activity should be observed, for instance, on day T5, T6. This symptom is normally diagnosed as parasympathetic overtraining, or Addisonic overtraining.

This phenomenon occurs when a level of fatigue exceeds a limit and a body senses a life threatening condition, the amount of the parasympathetic nerve activity increases to rest the body regardless of a will of a person. The body may feel such a life threatening condition when training in which loads to the body sharply increase is performed under a condition that fatigue builds up in the body.

An impact of training on a body, a level remaining physical strength, or a level of recovery can be determined based on connections between the training conditions and the amount of autonomic nerve activity during sleep. Signs or symptoms of overtraining also can be detected based on the connections. The amount of autonomic nerve activity can be measured by analyzing pulse waves.

Figure 1:
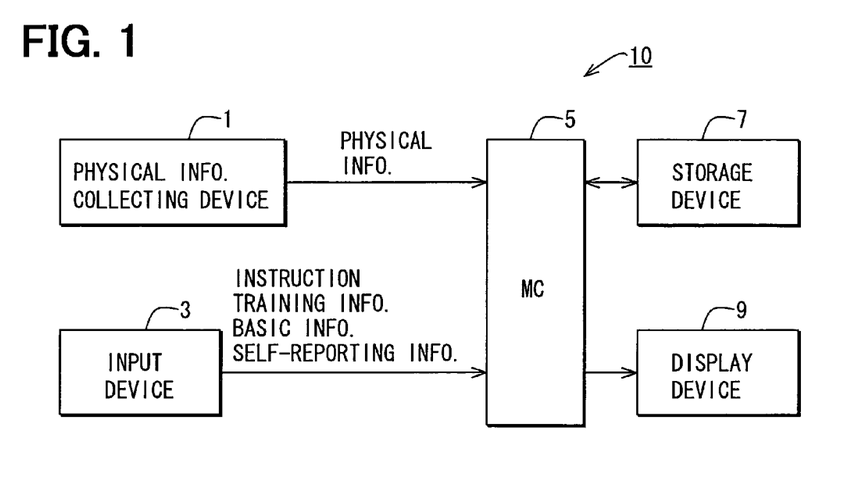
FIG. 1 is a block diagram of a physical condition monitoring system according to an embodiment of the present invention.

Referring to FIG. 1, a physical condition monitoring system 10 includes a physical information collecting device 1, an input device 3, a microcomputer (MC) 5, a storage device 7, and a display device 9. The physical information collecting device 1 collects physical information that indicates physical conditions of a subject during sleep, including heat rates, blood pressures, respiration rates, and body movements. The input device 3 includes a keyboard and a pointing device for inputting instructions for operating the system 10 and information on training.

The MC 5 produces indexes for overtraining determination based on the information inputted from the physical information collecting device 1 and the input device 3. It executes processes, such as a process for determining overtraining based on the indexes. The storage device 7 stores information obtained through the physical information collecting device 1 or the input device 3 and results of the processes.

The display device 9 displays an information input screen, data stored in the storage device 7, and physical condition monitoring screen. The information input screen is provided for inputting information via the input device 3. The physical condition monitoring screen is provided for displaying information on physical conditions or information required for the overtraining determination or remarks (determination results). The information is displayed on the physical condition monitoring screen based on contents of the storage device 7 and the results of the processes performed by the MC 5.

The physical information collecting device 1 may be configured as a large-size system installed in a room or as a portable device having an optical pulse wave sensor that uses light absorption characteristic of blood component. It may be configured to connect with the MC 5 via a signal line at all times or only when the collected physical information is transmitted. The collected physical information may be transmitted to the MC 5 by radio or via a memory device, such as a memory card.

The input device 3 can be configured with a communication interface or a read-in device. The communication interface is for communicating with other devices, such as a computer and measurement devices, directly or via a network. The read-in device is for reading information from memory devices. With this configuration, the system 10 can receive necessary information via the communication interface or the read-in device.

The information inputted to the system 10 via the input device 3 includes training information and self-reporting information. The training information contains an indication to show whether training is performed, a training menu, performance, and heart rates and lactic acid levels in the blood during the training. The self-reporting information contains basic physical information including a body temperature and weight after waking up, an appetite, sleepiness, and tiredness.

The storage device 7 stores physical information during sleep produced in a process performed by the MC 5, sleep evaluation values and determination results in addition to the above-described information. The physical information contains the amount of autonomic nerve activity and the amount of body movement. The storage device 7 stores each day of such information for multiple days, for instance, the maximum of one year.

Figure 8:
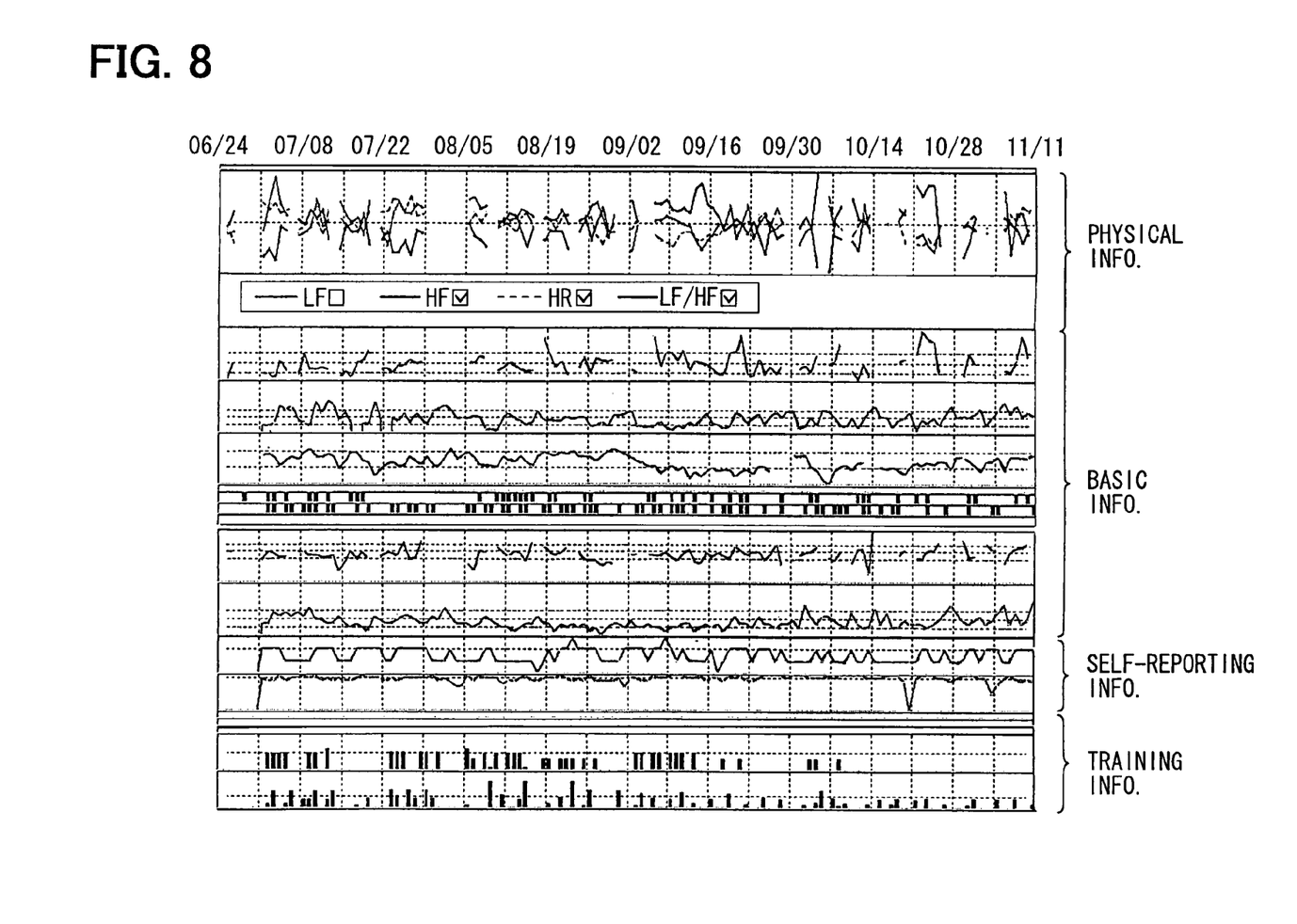
FIG. 8 is an example view of a physical condition monitoring screen according to the embodiment.

Specified terms of specified items of the information stored in the storage device 7 are displayed on the physical condition monitoring screen. An example of the physical condition monitoring screen is shown in FIG. 8. Three months of the physical information, the basic physical information, the self-reporting information, and the training information are shown in graphs with average values so that variations in the information are recognized. The physical information provides averages of the amounts of the autonomic nerve activity and heart rates during sleep per night. The basic physical information provides the body temperature and the weight. The self-reporting information provides physical conditions and appetites. The training information provides training levels.

Figure 2:
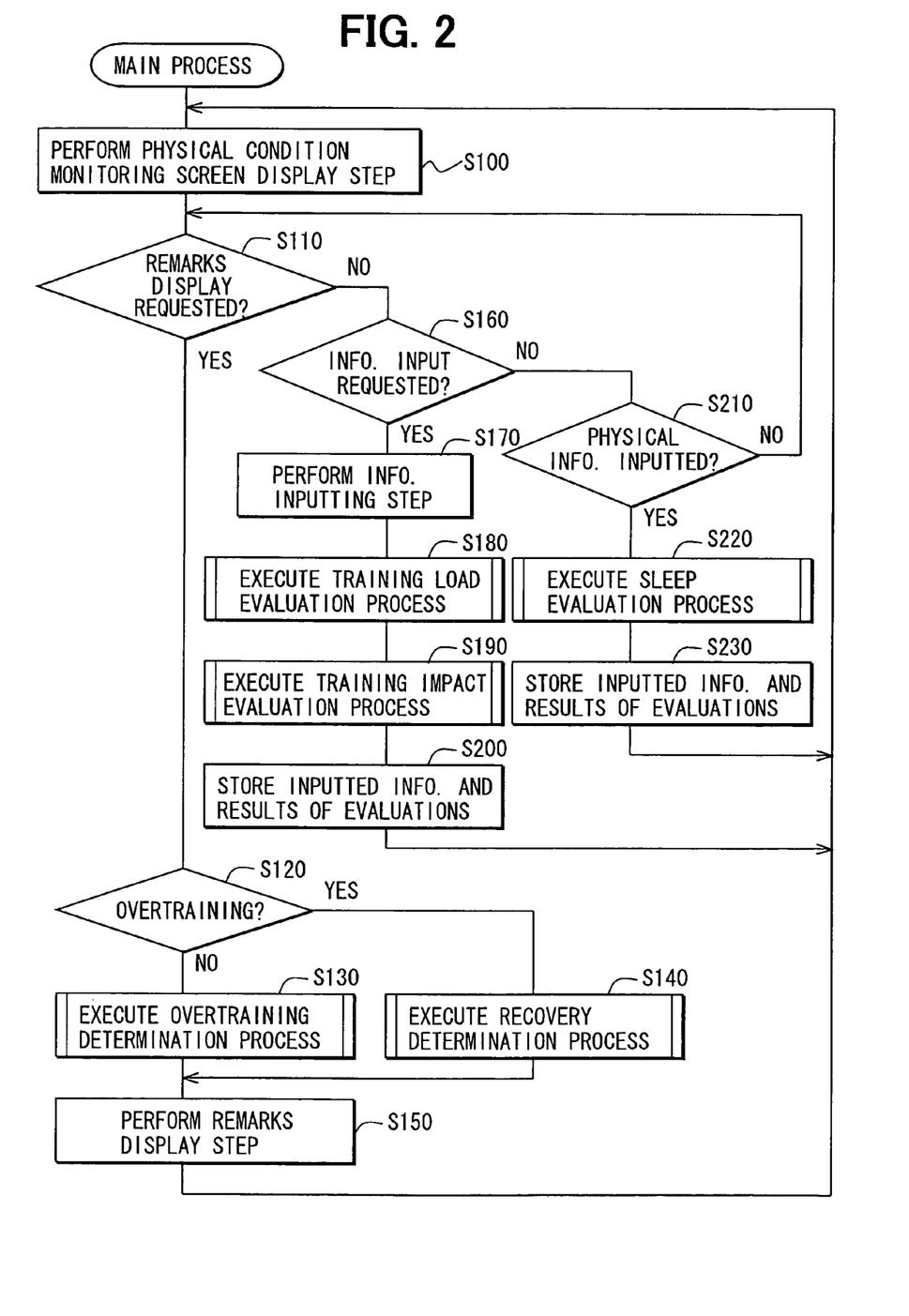
FIG. 2 is a flowchart of a main process performed in the physical condition monitoring system according to the embodiment.

The system 10 starts a main process shown in FIG. 2 when it is turned on. A step for displaying the physical condition monitoring screen on the display device 9 is performed (S100). Selections of Information items and terms to be displayed on the screen are made through the input device 3, more specifically, by selecting icons on the screen.

It is determined whether an instruction for requesting to display remarks on the physical condition of that day is inputted via the input device 3 (S110). It is determined whether an instruction for requesting to input information, such as the training information, is inputted via the input device 3 (S160). Then, it is determined whether the physical information is inputted from the physical information collecting device 1 (S210). If the results of the determination are all no, steps S110, S160, and S210 are repeated.

If the instruction for requesting to display the remarks is inputted and a result of the determination of step S110 is yes, it is determined whether determination of overtraining has been made (S120). If the determination of overtraining has not been made, an overtraining determination process is executed (S130). In the overtraining determination process, a remaining physical strength of the subject is determined. If the determination of overtraining has been made, a recovery determination process is executed (S140).

A remarks displaying process is executed for displaying remarks on the physical condition of the subject based on the results of the overtraining determination process and the recovery determination process on the display device 9 (S150). Then, the process returns to step S100. The remarks can be displayed in a specified area in the screen or in a separate window on the display device 9.

It is determined whether an instruction for requesting to input information has been inputted via the input device 3 (S160). If it has been inputted, that is, a result of step S160 is yes, an information inputting process is executed (S170). In the information inputting process, the information input screen is displayed on the display device 9 for receiving the information via the input device 3.

When the information input is completed, a training load evaluation process (S180) and a training impact evaluation process (S190) are executed. In the training load evaluation process, loads of the training of that day is evaluated based on the training information included in the inputted information. In the training impact evaluation process, impacts of the training on the body of the subject are evaluated. The results of the training load evaluation process and the training impact evaluation process are stored in the storage device 7 together with other information inputted in step S170 (S200). Then, the process returns to step S100.

The training load may be evaluated based on a training menu including kinds of training or the number of times of training, or the amount of exercise. The amount of exercise can be determined, for example, the number of strokes of arm swings, a range of the stroke, strides, duration of the exercise, and the amount of calorie consumed during the exercise, in the case of a runner.

The training impact may be evaluated based on the amount of change in physical conditions, such as changes in a heart rate and a lactic acid level in blood during the training. The physical condition of the subject is more precisely determined by referring to the training load or the exercise impact in addition to the physical information during sleep and the training information. As a result, the overtraining determination is more accurately performed.

The contents of the storage device 7 are updated and the updated information is reflected in the display of the physical condition monitoring screen. The evaluation results obtained in steps S180 and S190 are handled as items displayable on the monitoring screen in the same manner as other information stored in the storage device 7.

It is determined whether physical information has been inputted via the physical information collecting device 1 (S210). If the physical information has been inputted, that is, the result of step S210 is yes, a sleep evaluation process is executed based on the inputted physical information (S220). In this process, the physical information providing the physical conditions of the subject during sleep is produced and the sleeping conditions of that day are evaluated. Results of the sleep evaluation process are stored in the storage device 7 together with the inputted physical information. Then, the process returns to step S100.

Figure 3:
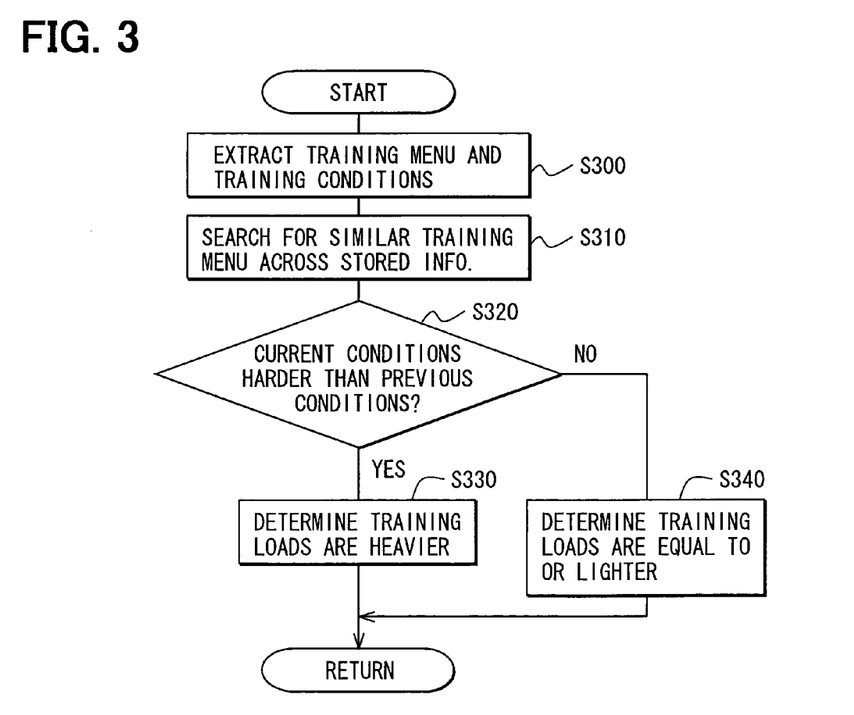
FIG. 3 is a flowchart of a training load evaluation process according to the embodiment.

The training load evaluation process is performed as shown in FIG. 3. When this process is started, a training menu and training conditions are extracted from the training information inputted in step S170 (S300). Information on conditions, including a running distance and the number of running times, when a training menu similar to the extracted training menu is performed, is searched for across the information stored in the storage device 8 (S310).

The training conditions contained in the currently inputted information is compared with the training conditions contained in the searched past information. It is determined whether the current conditions are harder than the previous conditions (S320). The training conditions are such as lap time and intervals. If the current conditions are harder than the previous conditions, it is determined that the training loads are heavier than the previous training (S330). If the current conditions are not harder that the previous conditions, it is determined that the training loads are equal to or lighter than the previous training (S340), and the process is completed.

Figure 4:
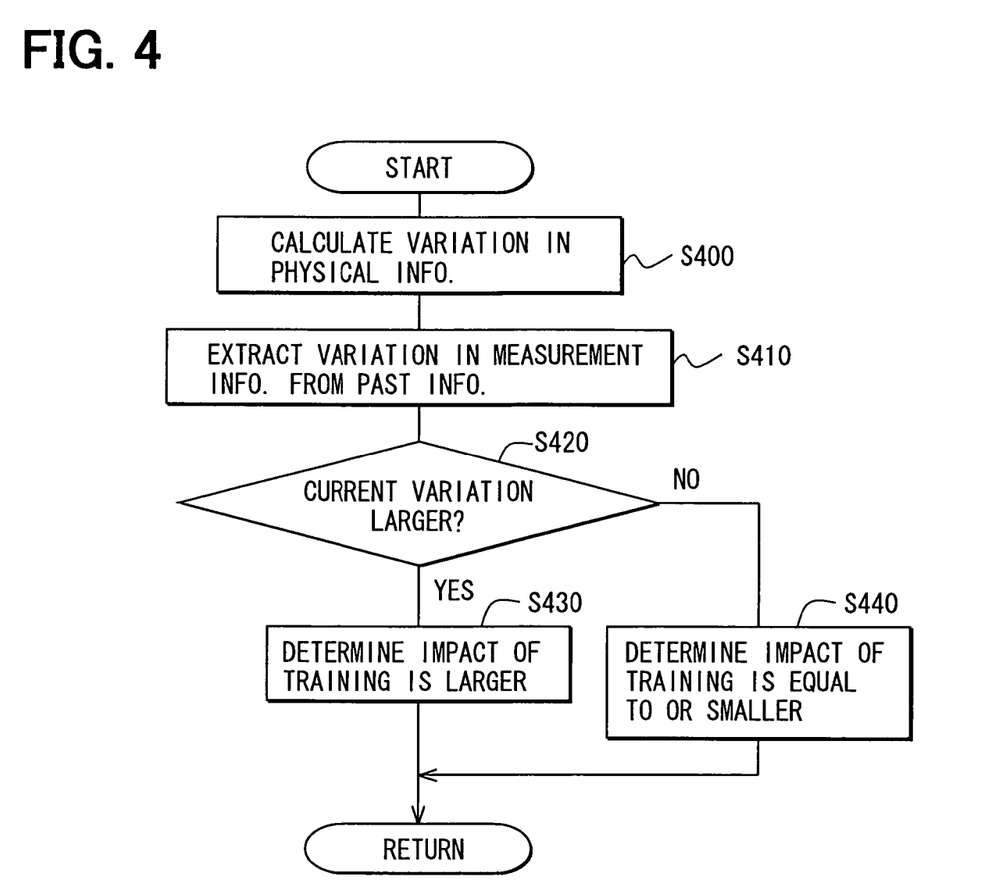
FIG. 4 is a flowchart of a training impact evaluation process according to the embodiment.

The training impact evaluation process is performed as shown in FIG. 4. When this process is started, physical information of the subject including measurements during training or before and after the training is extracted from the training information inputted in step S170. The physical information contains heart rates and the lactic acid levels in the blood. A variation in the physical information is calculated (S400). A variation in the measurement information is extracted in step S310 from the information on the conditions when a training menu similar to the extracted training menu is performed (S410).

The variation obtained in step S400 is compared with the variation obtained in step S410, and it is determined the current variation is larger then the previous variation (S420). If the current variation is larger than the previous variation, it is determined that an impact of the current training is larger than the previous training (S430). If the current variation is equal to or smaller than the previous variation, it is determined that the impact of the current training is equal to or smaller than the previous training (S440). Then, this process is completed.

Figure 5:
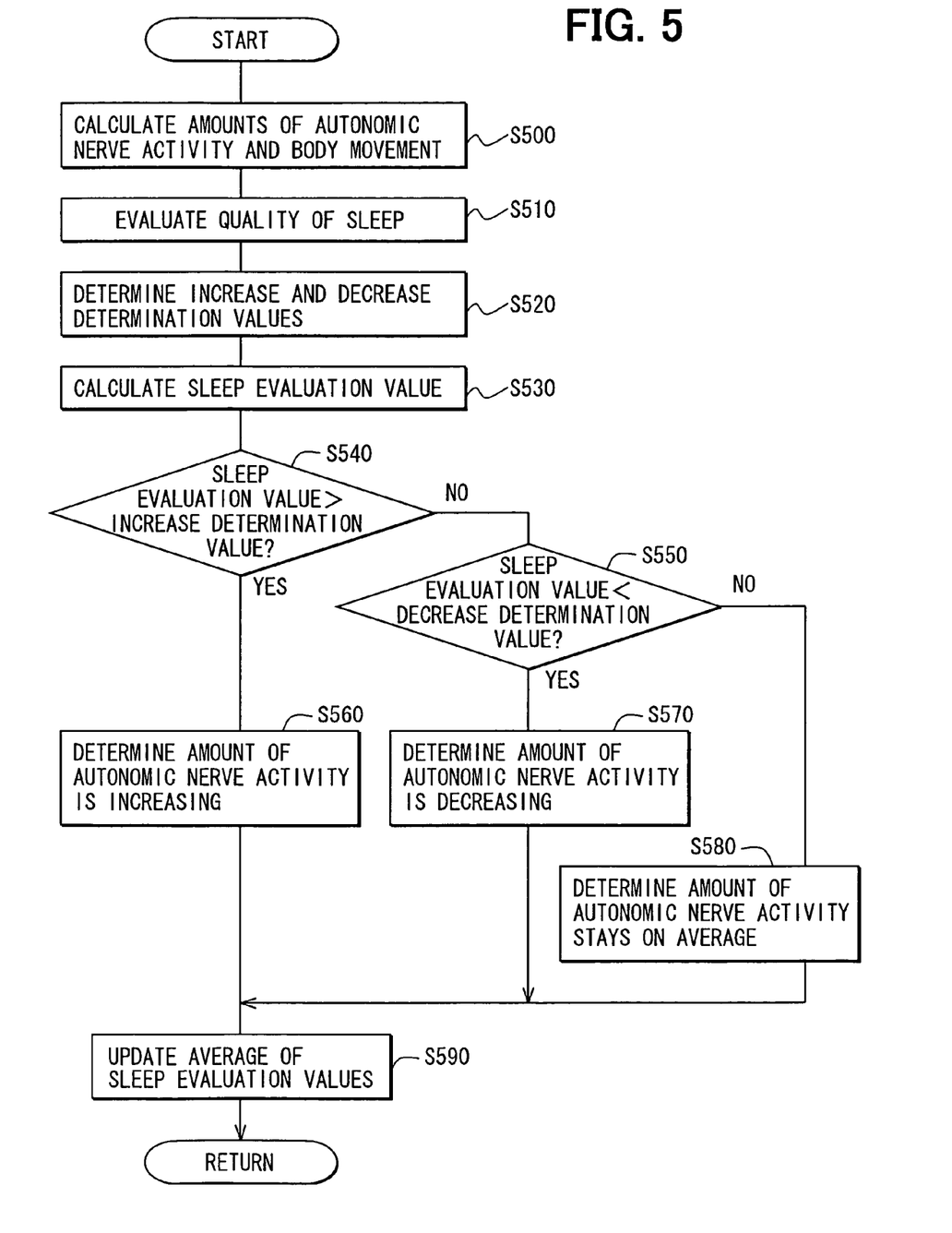
FIG. 5 is a flowchart of a sleep evaluation process according to the embodiment.

The sleep evaluation process is performed as shown in FIG. 5. Body movements occur during sleep due to mid-night awakening or other facts when the depth of sleep is shallow. When the amount of the body movements is large and a quality of sleep is low, namely, the subject is not in deep sleep, the subject will not obtain sufficient body rest or body recovery through sleep. Therefore, fatigue is more likely to build up in the subject. By evaluating the quality of sleep and adjusting a threshold for the overtraining determination so that determination indicating that care is required is more likely to be made when the quality of sleep is low, overtraining is properly detected.

When this process is started, the amounts of autonomic nerve activity, the amount of body movement, and the heart rate during sleep are calculated based on the physical information inputted from the collecting device 1 (S500). The amounts of autonomic nerve activity include the amount of sympathetic nerve activity and the amount of parasympathetic nerve activity. These amounts may be calculated for a whole night or for specific at certain times of the night, at which the subject might be in a deep sleep, falling asleep, and in the later half of the sleep. The calculated amounts may be averages or cumulative amounts at the times and the maximum values, the minimum values, and variations per unit time may be taken into consideration.

A quality of sleep, that is, the depth of sleep, is evaluated based on the calculated amount of the body movement (S510). The size of the body movement may be taken into consideration. An increase determination value and a decrease determination value are determined (S520). The increase determination value and the decrease determination value are thresholds for determining an increase and a decrease in the amount of the autonomic nerve activity, respectively, based on the evaluated quality of sleep. They are set for the amount of sympathetic nerve activity and the amount of parasympathetic nerve activity, respectively. More specifically, they are set based on last several days of the sleep quality evaluations so that they become smaller as the quality of sleep is lower. When the quality of sleep is low, the subject may not fully recover from fatigue through sleep.

Sleep evaluation values are calculated for the amount of the sympathetic nerve activity and the amount of parasympathetic nerve activity, respectively (S530). The sleep evaluation values are calculated by subtracting an average of the last several days of the amount of the autonomic nerve activity from the amounts of the autonomic nerve activity calculated in step S500.

It is determined whether the sleep evaluation value is larger than the increase determination value set in step S520 (S540). If the sleep evaluation value is larger, it is determined that the amount of the autonomic nerve activity is decreasing (S560). If the sleep evaluation value is equal to or smaller than the increase determination value, it is determined whether the sleep evaluation value is smaller than the decrease determination value set in step S520 (S550). If it is smaller, it is determined that the amount of autonomic nerve activity is decreasing (S570). If the sleep evaluation value is equal to or larger than the decrease determination value, it is determined that the amount of the autonomic nerve activity stays on the average (S580). After the completion of the determination, the average of the sleep evaluation values is updated with the present sleep evaluation value (S590) and this process is completed.

In this process, it is determined the amount of autonomic nerve activity is in an average condition, in an increasing condition, or a decreasing condition. Furthermore, the quality of sleep is determined based on the amount of body movement and the increase determination value is set at a lower value when the quality of sleep is low so that the amount of the autonomic nerve activity is more likely to be determined as in the increasing condition. The thresholds may be adjusted based on the evaluated quality of sleep of the previous day or preferably based on that of consecutive days.

Figure 6:
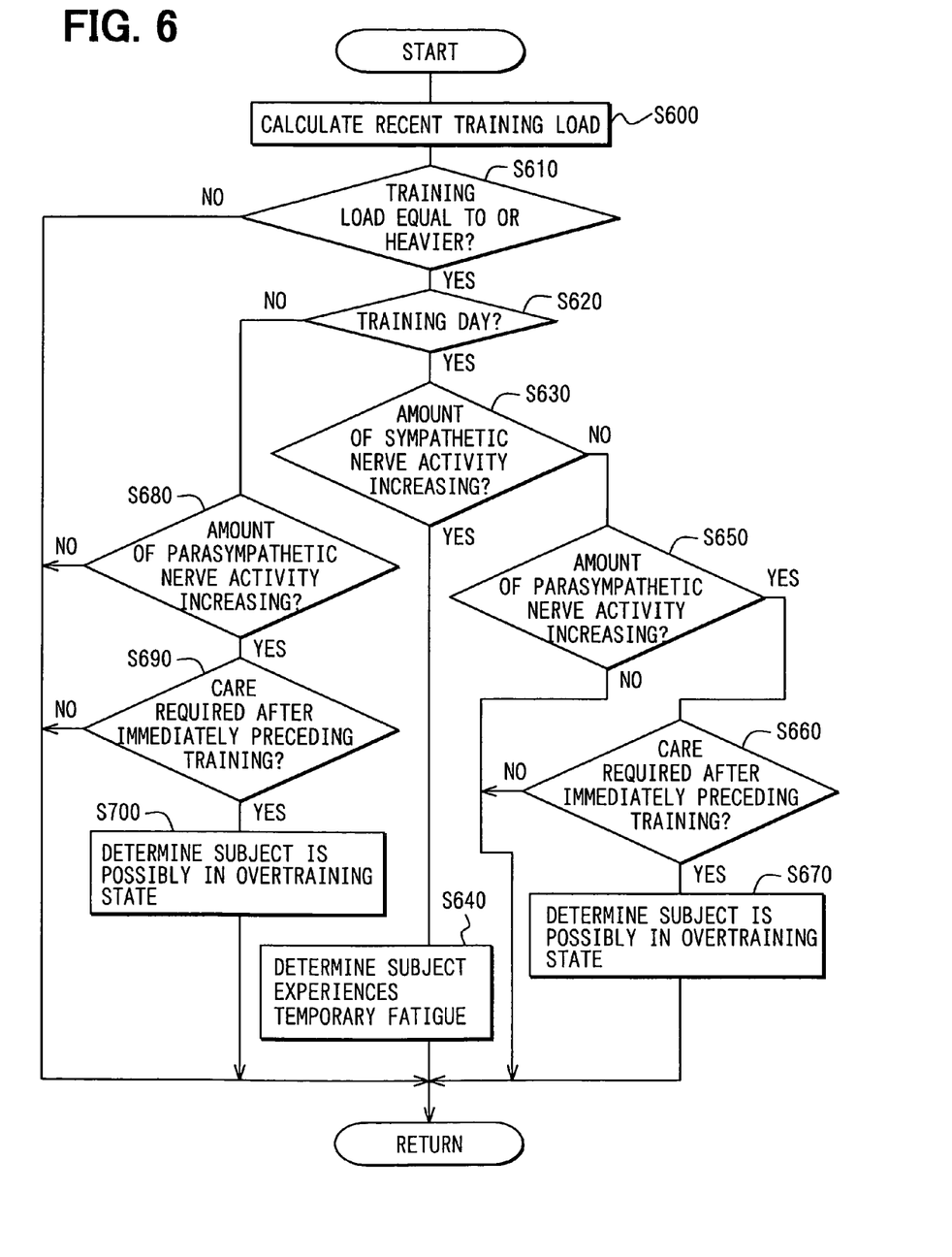
FIG. 6 is a flowchart of an overtraining determination process according to the embodiment.

The overtraining determination process executed in step S130 is performed as shown in FIG. 6. When this process is started, the training load of the last several days including a target day of the overtraining determination is calculated based on the training information stored in the storage device 7 (S600). Then, it is determined whether the calculated training load is equal to or heavier than a predetermined value (S610). If the recent training load is lighter than the predetermined value, it is determined that an excessive load is not applied to the body and therefore it is not necessary to perform the overtraining determination. Then, the process is terminated. If the recent training load is equal to or heavier than the predetermined value, it is determined whether the information used for the overtraining determination relates to a training day based on the training information inputted in step S170 (S620).

If the information relates to the training day, it is determined whether the amount of the sympathetic nerve activity during sleep is increasing based on the evaluation result obtained in step S220 (S630). If the amount of the sympathetic nerve activity is increasing, it is determined that the subject experiences temporary fatigue and care is required (S640). Then, this process is terminated.

If the amount of sympathetic nerve activity during sleep is not increasing, it is determined whether the amount of parasympathetic nerve activity during sleep is increasing (S650). If it is not increasing, it is determined that no sign or symptom is confirmed in the subject, and this process is terminated. If it is increasing, it is determined whether a result of the overtraining determination regarding the previous training day indicates that care is required (S660). If the result indicates that care is required, possible overtraining is determined, that is, the subject may have a severe injury (S670). Then, this process is terminated. If the result of the overtraining determination does not indicate that care is required, it is determined that the increase in the amount of the sympathetic nerve activity is caused by other factors. Then, this process is terminated.

If the information used in the determination is not related to a training day, namely, related to a resting day, it is determined whether the amount of the parasympathetic nerve activity during sleep is increasing (S680). If it is not increasing, it is determined that no sign or symptom of the overtraining is confirmed in the subject, and this process is terminated.

If the amount of the parasympathetic nerve activity is increasing, it is determined whether a result of the overtraining determination regarding the previous training day indicates that care is required (S690). If the result indicated that care is required, possible overtraining is determined (S700), and this process is terminated. If the result indicates that the care is not required, it is determined that the increase in the parasympathetic nerve activity is caused by other factors, and this process is terminated.

In this process, it is determined that the subject experiences temporary fatigue and care is required when an increase in the amount of sympathetic nerve activity is confirmed during sleep on the training day. The increase in the amount of sympathetic nerve activity is a sign of overtraining. If an increase in the amount of parasympathetic nerve activity is confirmed on the resting day immediately after the training day on which it is determined that care is required, probable overtraining is determined. An increase in the amount of parasympathetic nerve activity indicates a symptom of an early stage of overtraining.

Probable overtraining is also determined when a reverse phenomenon is observed in the amount of autonomic nerve activity on a training day immediately after the day on which it is determined that care is required. The reverse phenomenon observed in the amount of autonomic nerve activity indicates a symptom of a late stage of overtraining.

Overtraining is less likely to be developed by adjusting the amount of training when temporary fatigue is detected. Even when the overtraining is developed, it is properly detected without delay. Thus, immediate and proper treatment can be provided for the subject in an overtraining condition.

Figure 7:
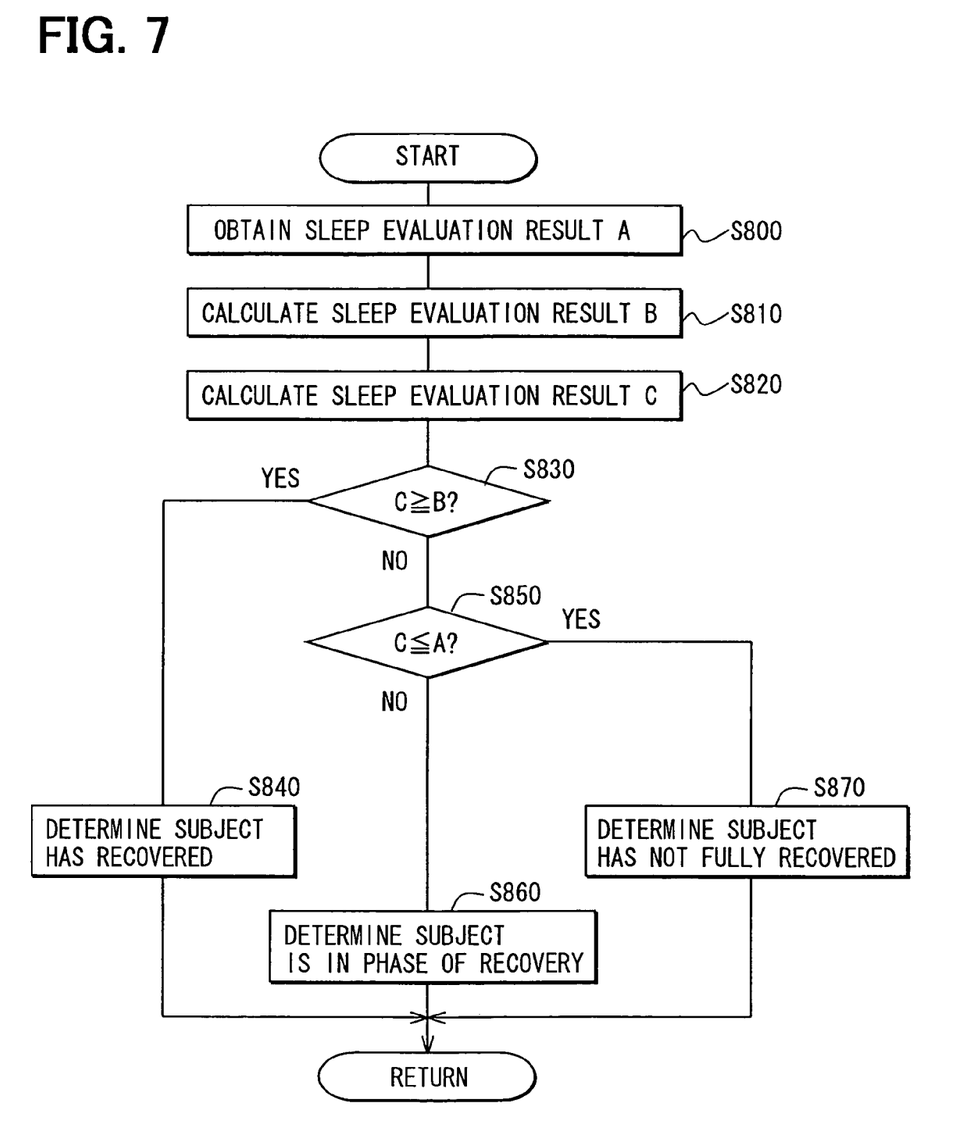
FIG. 7 is a flowchart of a recovery determination process according to the embodiment.

The recovery determination process executed in step S140 is performed as shown in FIG. 7. Irregularities occur in the physical information during sleep, for instance, in the amount of autonomic nerve activity, when the subject is in the overtraining condition. Therefore, a level of recovery from overtraining can be determined by observing the irregularities. A full recovery is determined when the irregularities disappear and the physical information returns to the condition before the determination of overtraining.

When this process is started, the sleep evaluation value related to the amount of the sympathetic nerve activity when the overtraining is determined is obtained (S800). This sleep evaluation value is referred to as a sleep evaluation result A. An average of the sleep evaluation values related to the amount of the sympathetic nerve activity before the overtraining is calculated (S810). The average of the sleep evaluation values is referred to as a sleep evaluation result B. Moreover, an average of the sleep evaluation values regarding the last several days of the amount of the sympathetic nerve activity after the day of the determination of overtraining is calculated (S820). The average of the sleep evaluation values is referred to as a sleep evaluation result C.

It is determined whether the recent sleep evaluation result C is equal to or higher than the previous sleep evaluation result B (S830). If it is equal to or higher, it is determined that the subject has recovered from the overtraining (S840), and this process is terminated. If the sleep evaluation result C is lower than the sleep evaluation result B, it is determined whether the sleep evaluation result C is equal to or lower than the sleep evaluation result A (S850). If it is equal to or lower, it is determined that the subject has not fully recovered from the overtraining (S870). If it is higher, it is determined that the subject is in a phase of recovery from the overtraining (S860), and this process is terminated.

In this process, a level of recovery from overtraining is determined based on whether the amount of the sympathetic nerve activity has returned to a level before the overtraining. When the subject is in an overtraining condition, a decrease in the amount of the sympathetic nerve activity during sleep is observed. However, an increase in the amount of the parasympathetic nerve activity during sleep is also observed when the subject is in the overtraining condition. Therefore, the level of recovery can be determined based on whether the amount of the parasympathetic nerve activity has returned to a level before the overtraining.

To improve accuracy of the overtraining determination, it is determined whether the predetermined amount or more of training is performed for a predetermined period. The overtraining determination is performed only when the predetermined amount or more of training is performed for the predetermined period. The amount and the period of training are determined based on the training information obtained from the input device 3.

Overtraining occurs when heavy loads are applied to the body in a condition that fatigue has been built up in the body. The amount of autonomic nerve activity used as an index for the determination of overtraining varies according to various factors other than fatigue. Thus, improper overtraining determination is less likely to occur by performing the overtraining determination only when heavy loads are applied to the body in a condition that fatigue has been built up in the body.

Furthermore, the level of recovery can be determined based on both the amount of the sympathetic nerve activity and the amount of parasympathetic nerve activity. In the remarks displaying process (S150) executed after the overtraining determination process (S130) or the recovery determination process (S140), the results of determination performed in steps S640, S670, S700, and S850 through 870 are displayed as remarks.

The physical condition monitoring system 10 displays the physical condition monitoring screen. In the monitoring screen, various kinds of information inputted through the physical information collecting device 1 or the input device 3 are provided such that connections between them are indicated. When the amount of the sympathetic nerve activity during sleep, the training conditions, the training loads, and training impacts are displayed on the screen, connections between them are clearly confirmed. Physical conditions of the subject, that is, an athlete under monitoring, or recovery conditions after overtraining are properly determined based on the confirmed connections. The amount of the sympathetic nerve activity is used as an index for evaluating a physical recovery after the training and a relaxation level. The training conditions, the training loads, and the training impacts are used as indexes for evaluating the amount of load applied to the body and the tiredness. Therefore, sings or symptoms of overtraining can be properly detected based on the connections.

In the physical condition monitoring system 10, sings and symptoms of the overtraining are determined based on the amount of the sympathetic nerve activity during sleep and the training conditions or loads. Then, results of the determinations are displayed as remarks. The connections between the amount of the sympathetic nerve activity and the training conditions or the loads may not be understood. However, the conditions of the subject are properly indicated with the remarks and therefore the overtraining syndrome is less likely to be developed in the subject.

Moreover, the quality of sleep is evaluated based on the amount of the body movement during sleep. If the quality of sleep is low, fatigue is more likely to be built up in the subject. In this case, the increase determination value for the evaluation of the amount of the autonomic nerve activity is adjusted so that the result of the determination is more likely to indicate that care is required. As a result, a development of the overtraining syndrome is effectively reduced.

The physical information collecting device 1, the input device 3, the storage device 7, and the display device 9 correspond to physical information collecting means, training information collecting means, storage means, and display means, respectively. The overtraining determination process (S130) corresponds to physical condition determining means.

Steps S630 and S640 of the overtraining determination process (S130) correspond to fatigue detecting means. Steps S650 through S700 of the overtraining determination process (S130) correspond to overtraining detecting means. The recovery determination process (S140) corresponds to recovery determining means. Steps S510 and S520 of the sleep evaluation process (S220) correspond to threshold adjusting means. The training load evaluation process (S180) and the training impact evaluation process (S190) are load evaluating means and training impact evaluating means, respectively.

The present invention should not be limited to the embodiment previously discussed and shown in the figures, but may be implemented in various ways without departing from the spirit of the invention. For example, the training information may be inputted through portable sensors attached to the subject for detecting the heart rate and the movement of the body. Then, the training information is collected based on the information inputted from the sensors including the training loads and effects. The sensors include in the physical information collecting device 1 may be also used for collecting information on the training.

The physical information collecting device 1 and the input device 3 are preferably implemented by a single device. Specifically, the physical information collecting device 1 and the input device 3 are included in an information collecting device that detects pulse waves. The physical information during sleep, including a pulse rate or the amount of autonomic nerve activity, is obtained from pulse rate components of the pulse waves.

Moreover, the amount of body movement, which is contained in the physical information during sleep, and the training loads, which are contained in the training information, are obtained from the body movement component of the pulse waves. Pulse rates can be used instead of heart rates.

What is claimed is:

1. A physical condition monitoring system comprising:
   physical information collecting means for collecting physical information indicating a physical condition of a subject during sleep analyzed from a pulse wave, wherein the physical information includes at least an amount of autonomic nerve activity, wherein the autonomic nerve activity is at least one of sympathetic nerve activity and parasympathetic nerve activity;
   training information collecting means for collecting training information indicating a training condition;
   display means for displaying the physical information obtained through the physical information collecting means and the training information obtained through the training information collecting means in a manner that a connection between the physical information and the training information is indicated; and
   fatigue detection means for detecting temporary fatigue based on whether an increase in the amount of sympathetic nerve activity is confirmed on a training day.

2. The physical condition monitoring system according to claim 1, further comprising storage means for storing a plurality of days of the physical information and the training information, wherein
   the display means displays a plurality of days of the physical information during sleep and the training information, stored in the storing means, in a manner that variations in the physical information and the training information over a plurality of days are recognized.

3. The physical condition monitoring system according to claim 1, further comprising physical condition determining means for determining a physical condition of the subject, wherein
   the display means displays a result of determination, the determination performed by the physical condition determining means, together with the physical information during sleep and the training information.

4. The physical condition monitoring system according to claim 3, wherein the physical condition determining means includes fatigue detecting means that detects temporary fatigue for determining whether care is required for the subject.

5. The physical condition monitoring system according to claim 4, wherein the physical condition determining means performs the physical condition determination when a predetermined amount or more of training is performed for a predetermined period.

6. The physical condition monitoring system according to claim 1, wherein the physical information contains at least a heart rate.

7. The physical condition monitoring system according to claim 1, wherein the physical information contains at least a pulse rate.

8. The physical condition monitoring system according to claim 1, further comprising training load evaluation means that evaluates an amount of load of the training based on the training information, wherein
   the display means displays the amount of load in a manner that connections between the amount of load, the physical information, and the training information are indicated.

9. The physical condition monitoring system according to claim 1, further comprising training impact evaluation means that evaluates an impact of training on the subject based on the training information, wherein
   the display means display the impact of training in a manner that connections between the impact of training, the physical information, and the training information are indicated.

10. The physical condition monitoring system according to claim 1, wherein the physical information collecting means and the training information collecting means are implemented by a single information collecting device.

11. A physical condition monitoring system comprising:
    physical information collecting means for collecting physical information indicating a physical condition of a subject during sleep analyzed from a pulse wave, wherein the physical information includes at least an amount of autonomic nerve activity, wherein the autonomic nerve activity is at least one of sympathetic nerve activity and parasympathetic nerve activity;
    training information collecting means for collecting training information indicating a training condition;
    display means for displaying the physical information obtained through the physical information collecting means and the training information obtained through the training information collecting means in a manner that a connection between the physical information and the training information is indicated; and
    overtraining detecting means that detects possible overtraining based on the amount of autonomic nerve activity.

12. The physical condition monitoring system according to claim 11, wherein the overtraining detecting means detects possible overtraining based on an increase in the amount of parasympathetic activity on a resting day.

13. The physical condition monitoring system according to claim 11, wherein the overtraining detecting means detects possible overtraining based on a decrease in the amount of sympathetic activity and an increase in the amount of parasympathetic activity on a training day.

14. The physical condition monitoring system according to claim 11, further comprising: recovery determining means that determines a level of recovery from overtraining after the detection of the possible overtraining based on the physical information during sleep obtained before and at the detection of possible overtraining.

15. The physical condition monitoring system according to claim 11, wherein:
   the physical information collecting means obtains an amount of body movement during sleep as an item of the physical information;
   further comprising:
      sleep quality evaluation means that evaluates a quality of sleep based on the amount of body movement; and
      threshold adjustment means that adjusts a threshold used for determining whether the amount of the autonomic nerve activity is increasing based on the evaluation of quality of sleep.

* * * * *